US006525303B1

(12) United States Patent
Gladnick

(10) Patent No.: US 6,525,303 B1
(45) Date of Patent: Feb. 25, 2003

(54) CONTROL SYSTEMS AND METHODS FOR SYNCHRONIZING DIFFUSE ILLUMINATION WITH A CAMERA

(75) Inventor: Paul G. Gladnick, Seattle, WA (US)

(73) Assignee: Mitutoyo Corporation, Kawasaki (JP)

( * ) Notice: Subject to any disclaimer, the term of this patent is extended or adjusted under 35 U.S.C. 154(b) by 0 days.

(21) Appl. No.: 09/401,654

(22) Filed: Sep. 23, 1999

(51) Int. Cl.⁷ .............................................. H01L 27/00
(52) U.S. Cl. ................... 250/208.1; 250/234; 250/204; 250/216
(58) Field of Search ............................. 250/208.1, 204, 250/205, 234, 216, 559.16–559.18

(56) References Cited

U.S. PATENT DOCUMENTS

| | | | |
|---|---|---|---|
| 4,567,551 A | 1/1986 | Choate | 362/398 |
| 4,706,168 A | 11/1987 | Weisner | 362/18 |
| 4,729,070 A | 3/1988 | Chiu | 362/33 |
| 4,893,223 A | 1/1990 | Arnold | 362/252 |
| 5,038,258 A | 8/1991 | Koch et al. | 362/237 |
| 5,141,321 A | * 8/1992 | Tsuruoka | 356/400 |
| 5,307,207 A | 4/1994 | Ichihara | 359/622 |
| 5,690,417 A | 11/1997 | Polidor et al. | 362/244 |
| 5,753,903 A | 5/1998 | Mahaney | 250/205 |
| 6,044,170 A | * 3/2000 | Migdal et al. | 382/154 |

* cited by examiner

Primary Examiner—Que T. Le
Assistant Examiner—Thanh X. Luu
(74) Attorney, Agent, or Firm—Oliff & Berridge, PLC

(57) ABSTRACT

A light pattern controller generates a pattern of continuous wave, modulated and/or pulsed light onto a face of a collimating element. The light beam is collimated by the collimating element and extends to a focusing element which focuses the collimated light onto an illumination field. A controller controls the light pattern controller or the light source to determine a shape of the pattern on the face of the collimating element. The illumination field is imaged by an electronic or digital camera having first and second fields. Each field captures an image by integrating light received from the illumination field over an integration period. The controller controls the light pattern controller and the light source, and/or the camera to ensure an even amount of illumination from each element of the light pattern focused on the illumination field is integrated by each field of the camera. The controller also controls the frequency, phase angle and pulse width of the light source.

22 Claims, 11 Drawing Sheets

CONTROL SYSTEMS AND METHODS FOR SYNCHRONIZING DIFFUSE ILLUMINATION WITH A CAMERA

BACKGROUND OF THE INVENTION

1. Field of Invention

This invention relates to systems and methods to generate diffuse illumination. In particular, this invention is directed to synchronizing a diffuse light source with an electronic or digital camera for a machine vision system.

2. Description of Related Art

Uniform, diffuse illumination of a sample part is often necessary in commercial vision systems to accentuate an edge of the sample part within a designated field of view. Since most sample parts are not transparent, diffuse illumination of the sample part is also necessary so that light which is reflected from the sample part can be collected by an imaging system. Furthermore, an adjustable diffuse illumination source accommodates sample parts having a wide variety of shapes.

Typically, the intensity of light emitted by a light source is adjustable when the magnification of the imaging system is also adjustable. The adjustable illumination provides the ability to illuminate sample parts having different characteristics, such as, for example, shape, composition, and surface finish.

Also, conventional light sources project light onto the sample part at an angle from a plane which is normal to the imaging plane. This angle is referred to as the angle of incidence. Light projected at an angle of incidence which is between 0 and 90 degrees may improve the surface contrast of the image and also more clearly illuminate textured surfaces. Typically, such light sources have a prescribed range for the angle of incidence. Conventionally, the angle of incidence varies between 10° and 70° relative to the plane that is normal to the optical axis of the imaging system. Such a range is relatively broad and, therefore, provides adequate contrast in an image of a sample part.

Furthermore, conventional vision systems can also adjust the circumferential position of the source of diffuse lighting about an optical axis. Typically, the position of the diffuse lighting source is adjustable in, for example, addressable sectors or quadrants. As such, any combination of sectors and quadrants of such a circular light pattern can be illuminated. Additionally, the intensity level of the light source can be coordinated with the circumferential position of the light source to optimize the illumination of a sample part edge.

For example, some conventional vision systems include an annular light source that emits rectangular or toroidal patterns. The light source is an annulus which is divided into four quadrants. Also, other conventional vision systems include a ring light having an annulus which is subdivided into eight sectors. Additionally, some conventional vision systems have hemispherically-shaped light sources to direct light from a multitude of positions relative to an optical axis. The center of the hemisphere serves as a focal point for the light sources. Furthermore, any combination of sectors and quadrants can simultaneously be illuminated with varying illumination levels.

SUMMARY OF THE INVENTION

Recently, manufacturers of conventional vision systems have started offering a solid-state replacement for the traditional tungsten filament lamp, e.g., a halogen lamp, that has been used in conventional diffuse light sources. These manufacturers now offer light emitting diodes (LEDs) that offer higher reliability, a longer service life, greater brightness, lower cost, good modulation capabilities and a wide variety of frequency ranges.

Some manufacturers of such conventional vision systems provide opto-electro-mechanical designs that partially achieve the characteristics of the conventional diffuse light sources discussed above. However, these opto-electro-mechanical devices are complicated, costly, lack versatility, and do not enhance a video inspection process. For example, these light sources require overly intricate mechanical motion which results in a lower vision system throughput and an increase in cost. Other conventional solid-state light sources require a large number of discrete light sources in a two-dimensional array and an elaborate electronic cross-bar to energize them. Furthermore, other conventional solid-state light sources must accommodate at least fifty discrete light sources in a three-dimensional array housed in a large carriage.

Accordingly, conventional diffuse light sources are incapable of providing a full-featured, reliable, inexpensive system and method to diffusely illuminate a sample part. Moreover, conventional diffuse light sources only marginally provide the capability to control the intensity, angle of incidence and circumferential position. Such conventional diffuse light sources do not optimally illuminate sample parts for dimensional measurements when varying construction (e.g., shape), material (e.g., absorptivity, scattering, etc.), and surface properties (e.g., color or texture) are involved.

This invention provides control systems and methods that achieve the diffuse lighting effects that are currently offered on the market.

This invention separately provides control systems and methods that achieve all these features using a single solid-state source or small number of solid-state sources, such as LEDs or laser diodes.

This invention separately provides control systems and methods that synchronize the illumination of a part with the frame capture timing of an electronic or digital camera.

This invention separately provides control systems and methods that allow a part to be illuminated from a desired phase angle and over a desired arc length that is synchronized with the frame capture timing of an electronic or digital camera.

This invention separately provides control systems and methods that allow intermittent illumination of a part to by synchronized with the frame capture timing of an electronic or digital camera.

This invention separately provides control systems and methods that create conventional as well as more versatile diffuse illumination using a simpler, more robust device.

This invention separately provides control systems and methods that allow the selection of illumination color.

This invention separately provides control systems and methods that preserve the high resolution necessary for dimensional metrology measurements without the unnecessary expense of electronic or digital color camera technology.

The control systems and methods of this invention provide an economically viable way to obtain color images by assembling RGB images from a monochrome electronic or digital camera. A monochrome electronic or digital camera provides the high spatial resolution that is necessary for dimensional measurements without using expensive electronic or digital color camera technology.

The control systems and methods of this invention synchronize the light source with the frame integration of the electronic or digital camera so that each pixel of the electronic imaging elements senses the same number of illumination strobes and/or sweeps. The control systems and methods of this invention synchronize the light source so that each pixel in the electronic or digital camera receives the same input intensity. The control systems and methods of this invention also synchronize the electronic or digital camera with the light beam.

Using the control systems and methods of this invention, the illumination color may be controlled based on the sample part properties (e.g., pigmentation) in order to improve image contrast. Also, illumination color selection is used to produce a high resolution color image using a monochrome electronic image detector. Thus, the systems and methods of this invention preserve the high resolution necessary for dimensional metrology measurements without the unnecessary expense of electronic or digital color camera technology.

Exemplary embodiments of the control systems and methods of this invention include a light pattern controller that includes a beam deflector that is mounted on a motor shaft. The beam deflector has a mirror. The beam deflector tilts in proportion to the centrifugal force exerted on the beam deflector when the motor shaft rotates. A light beam incident on the mirror is deflected by an angle which is defined by the tilt of the beam deflector.

Because the beam deflector is rotating, the deflected light beam sweeps out a cone. The deflected light beam cone is incident on a focusing element and sweeps out a circular pattern on the surface of the focusing element. The radius of the circular pattern is dependent on both the distance of the focusing element from the beam deflector and the angle at which the light beam is deflected. The greater the angle of deflection and the farther the focusing element is from the beam deflector, the larger the circular pattern becomes. Therefore, since the rotational speed of the motor shaft is directly proportional to the deflection angle and since the size of the circular pattern is directly proportional to the deflection angle, the size of the circular pattern is directly proportional to the rotational speed of the motor shaft.

The speed at which the light beam traverses the circular pattern is also directly proportional to the rotational speed of the motor shaft. Therefore, the rotational speed of the motor shaft controls both the size of the circular pattern and the speed with which the light beam traverses the light pattern. Thus, the motor and beam deflector control the light pattern.

The light beam is collimated by the focusing element to sweep out a column. This column of light is reflected by a mirror to be substantially parallel to and to surround an optical axis of an imaging device of a vision system. The imaging device, which may include a charge-coupled device (CCD), employs optical lenses to produce an image of a sample part positioned in a field of view and located at an object plane. The collimated pattern is focused onto the same field of view using another focusing element. Reflected and scattered light from the field of view is imaged onto the imaging device using optical lenses.

In other exemplary embodiments of the systems and methods of this invention, the light pattern controller includes a two-dimensional scanning galvanometer. The galvanometer is driven to deflect the light beam to sweep out a cone.

In other exemplary embodiments of the systems and methods of this invention, the light pattern controller includes a liquid crystal device. The liquid crystal device includes an array of addressable sectors that controllably block portions of the light from the light source from impinging on the collimator, or controllably reflect portions of the light from the light source to impinge on the collimator. The liquid crystal device of the light pattern controller controls the pattern of light from the light source that impinges on the collimator.

The control systems and methods of this invention control the circumferential position, sectors and/or quadrants of the source of diffuse lighting about the optical axis by turning the light source on as the light beam passes a first desired position and by turning the light source off as the light beam passes a second desired position. The position of the effective illumination source is determined by the first and second positions. Moreover, multiple effective illumination sources can be created by turning on and off the light source multiple times for each revolution of the beam deflector. The circumferential length of the sector of the illumination source illuminated is determined based on the amount of time that elapses between the time at which the light source is turned on and the time at which the light source is turned off. This timing is determined either by measuring the rotary speed and position of the motor shaft on which the beam deflector is mounted or by the signals driving the galvanometer. In both cases, pre-registration of the light beam angular location about the imaging system optical axis is known.

These and other objects of the invention will be described in or be apparent from the following description of the exemplary embodiments.

BRIEF DESCRIPTION OF THE DRAWINGS

The invention will be described in conjunction with the following drawings, in which like reference numerals designate like elements and wherein.

DETAILED DESCRIPTION OF PREFERRED EMBODIMENTS

Exemplary embodiments of the systems and methods of this invention incorporate the optical source monitoring described in U.S. patent application Ser. No. 09/220,705, incorporated herein by reference in its entirety. The optical source monitoring of the incorporated 705 application measures the real-time optical power output from the solid-state devices. This is possible on continuous or pulse operated systems. The measurements are taken so that power output variations may be corrected. Power output variations are due primarily to aging, drive current fluctuations and temperature drifts. The intensity measurements permit a level of calibration and instrument standardization which can yield reproducible illumination among an instrument model line.

Exemplary embodiments of the systems and methods of this invention also incorporate the systems and methods to generate diffuse illumination described in U.S. Pat. No. 6,334,699, incorporated herein by reference in its entirety. Exemplary embodiments of the systems and methods of this invention further incorporate the systems and methods to controllably generate illumination patterns described in U.S. patent application Ser. No. 09/323,916, incorporated herein by reference in its entirety.

Figure 1:
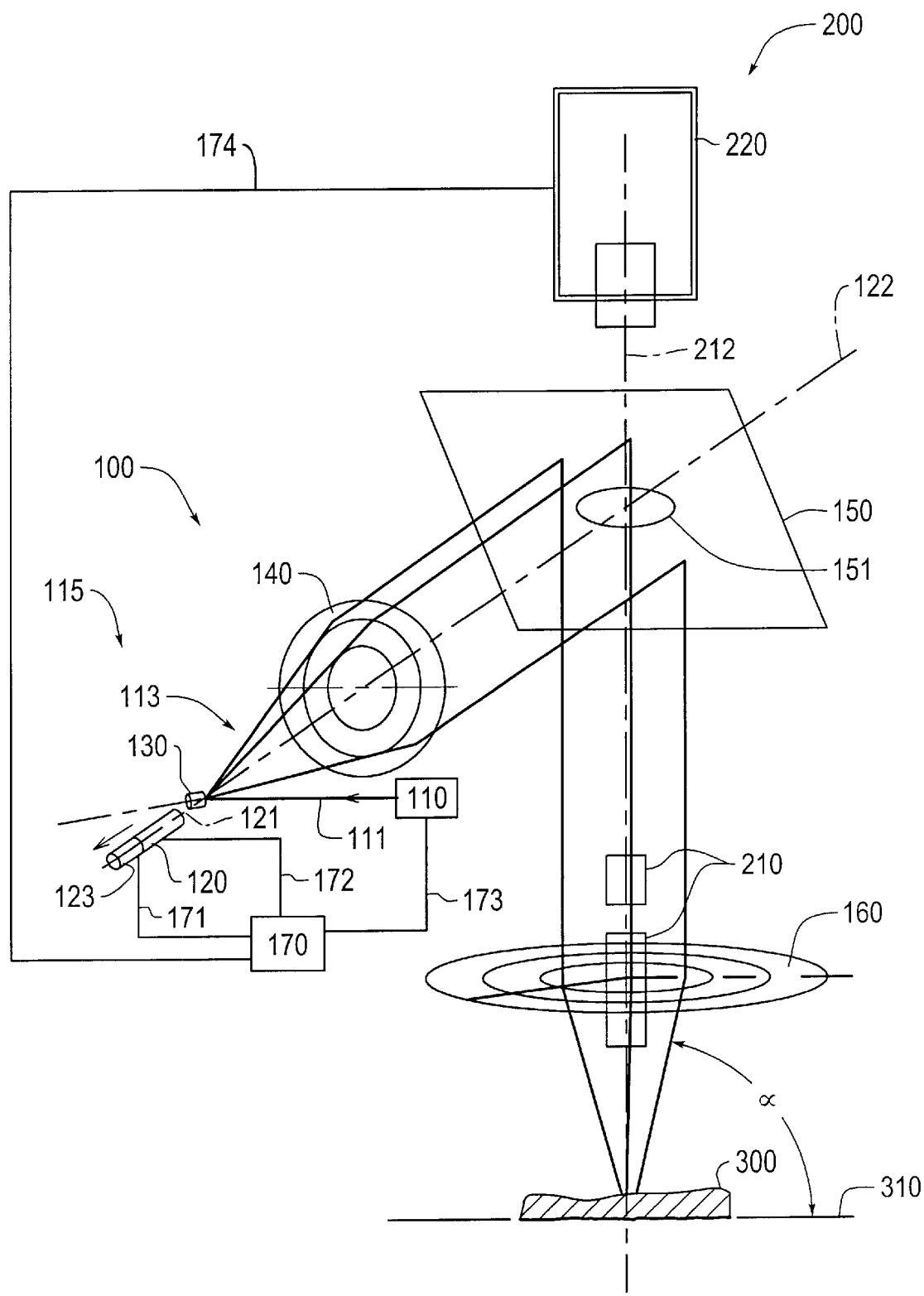
FIG. 1 is a schematic diagram of one exemplary embodiment of a diffuse lighting system according to this invention.

FIG. 1 is a schematic diagram of an exemplary diffuse illumination system 100 of this invention. The system 100 includes a light source 110 emitting a light beam 111, a light pattern controller 115, a collimator 140, a mirror 150, a focusing element 160 and a controller 170. The light pattern controller 115 includes a motor 120 and a beam deflector 130. FIG. 1 also shows an imaging system 200 that includes an electronic or digital camera 220 and an optical system 210 and that produces an image of a sample part 300. The system 100 illuminates the sample part 300 on an inspection plane 310 so that the imaging system 200 may obtain an image of the sample part 300.

The light source 110 has one or more solid-state light emitting devices that are stable and have a long service life. The solid-state light emitting devices may include LEDs, laser diodes or any other known or later developed solid-state light emitting structure. Further, the solid-state light emitting devices may emit radiation in the ultra-violet, visible and/or near-infrared regions of the electromagnetic spectrum. The solid-state light emitting devices are selected because they emit radiation in the spectral regions in which the electronic imaging elements, such as charge coupled devices, of the electronic or digital camera 220 are known to be photosensitive.

LEDs are also used as the solid-state light emitting devices because LEDs are more amenable to precise optical power regulation than halogen lamps. This is at least partially due to the smaller drive currents needed to operate the LEDs. In addition, the discrete nature of LEDs allows the wavelength of the emitted light to be more flexibly selected. Also, when driven electronically within the working parameters of the LEDs, the repeatability and reliability of the light output by the LEDs are both very high. In addition, some LEDs are capable of emitting light in the ultra-violet A frequency range, which improves the resolving power of imaging optics.

The light source 110 may have one or more optical power monitoring devices incorporated within the light source 110. Preferably, these devices are silicon photo-diodes whose spectral responsivity is matched to the spectral emission of the solid-state light emitting devices within the light source 110. These optical power monitoring devices are not restricted by material or design. Any known or later developed device capable of measuring the optical output of the solid-state light emitting devices within light source 110 can be used. In a configuration where the light source 110 can multiplex between different solid-state emitting devices that emit light of different illumination colors, each such solid-state light emitting device has a dedicated device to monitor optical power incorporated within light source 110.

As shown in FIG. 1, the light source 110 emits the light beam 111 that is incident on the beam deflector 130 of the light pattern controller 115. The beam deflector 130 is mounted on a shaft 121 of the motor 120 that is aligned with a transmitting axis 122. The beam deflector 130 tilts relative to the axis of the shaft 121 in proportion to the centrifugal force exerted on the beam deflector 130 when the motor shaft 121 rotates. As more clearly shown in FIG. 4, the light beam 111 from the light source 110 is directed onto a mirror 134 of the beam deflector 130 and is reflected from the mirror 134 at an angle that is defined by the tilt of the beam deflector 130.

Additionally, because the beam deflector 130 is rotating, the light beam 111 sweeps out a cone 113. The deflected light beam cone 113 is incident on the collimator 140 and sweeps out a circular pattern on the surface of the collimator 140. The collimator 140 may be, for example, a condenser lens, a Fresnel lens, or a set of reflective louvers, or any other known or later developed device capable of collimating the light cone 113. The radius of the circular pattern is dependent on both the distance of the collimator 140 from the beam deflector 130 and also the angle at which the light beam 111 is deflected by the beam deflector 130. The greater the angle of deflection and the farther the collimator 140 is from the beam deflector 130, the larger the circular pattern swept by the light beam 111 will be on the surface of the collimator 140. Therefore, since the deflection angle is directly proportional to the rotational speed of the motor shaft 121 and since the size of the circular pattern is directly proportional to the deflection angle, the size of the circular pattern is directly proportional to the rotational speed of the motor shaft 121.

Also, the speed at which the light beam 111 traverses the circular pattern is directly proportional to the rotational speed of the motor shaft 121. Therefore, the rotational speed of the motor shaft 121 controls both the size of the circular pattern and the speed with which the light beam 111 traverses the circular pattern. Thus, the light pattern controller 115 controls the pattern swept by the light beam 111 on the collimator 140.

The light cone 113 is collimated by the collimator 140 to sweep out a cylinder. The light cylinder is reflected by the mirror 150 to be substantially parallel to and to surround an optical axis 212 of the imaging system 200. The imaging system 200 employs optical lenses 210 to image a field of view located at an object plane onto the image plane of the electronic or digital camera 220. The collimated pattern is focused onto the same field of view using the focusing element 160.

The motor 120 may be a direct current motor (DC), an alternating current motor (AC) or a stepper motor. Any other known or later developed motor can also be used as the motor 120 to provide accurate rotational position and speed control information. Preferably, the speed control of the rotary motor should be better than 1%.

The mirror 150 is angled relative to the optical axis 212 and has an aperture 151 positioned where the optical axis 212 passes through the plane of the mirror 150. The aperture 151 is sized to permit unobstructed transmission of an image of the sample part 300 to the electronic or digital camera 220.

The cylinder of light is reflected by the mirror 150 toward the focusing element 160. The focusing element 160 can be a condenser lens, a Fresnel lens or the like. The focusing element 160 can also be a set of annular rings of mirrored louvers which are individually angled as a function of radius. The gradation in the angle of incidence of the light beam onto the sample part as a result of individual louvers or annular reflectors positioned at discrete radial locations in the focusing element 160 is discrete. It should be appreciated that any known or later developed element capable of collimating or focusing a light beam can also be used. It should also be appreciated that the collimator 140 may be identical to the focusing element 160.

The light beam 111 is directed by the focusing element 160 onto the sample part 300 on the inspection plane 310. The focusing element 160 has a focal distance which coincides with an average working distance of the objective lenses 210. For example, if the objective lenses 210 image at magnification levels of 1×, 3×, 5×, and 10× and have corresponding effective working distances of 59.0 mm, 72.5 mm, 59.5 mm, and 44.0 mm, respectively, with a resulting average working distance of 58.75 mm, then selecting a nominal focal length of approximately 59.0 mm for the focusing element 160 will coincide with the average working distance of the objective lenses 210 to yield good performance within the operational magnification range.

The controller 170 communicates with an encoder and/or tachometer 123 for the motor 120 over a signal line 171. The controller 170 receives angular position and/or speed data over the signal line 171 from the encoder and/or tachometer 123. The controller 170 also communicates with the motor 120 over a signal line 172. The controller 170 sends a drive signal to the motor 120 over the signal line 172. The controller 170 controls the phase and speed of the motor 120 by comparing the position and/or speed data received over the signal line 171 with predetermined position and/or speed values and makes changes to the drive signal sent to the motor 120 over the signal line 172 until the position and/or speed data received over the signal line 171 substantially match the desired values. The controller 170 controls the speed of the motor 120 in accordance with a desired angle of incidence.

The controller 170 also communicates with the light source 110 over a signal line 173. The controller 170 adjusts the on/off timing of the light source 110 based on the position and/or speed of the motor 120. The drive timing of the light source 110 is adjusted to the phase of the motor 120 to control the number of illumination sectors in an illumination field. The controller 170 also adjusts the drive timing of the light source 110 to determine the width of the illumination sector in the illumination field.

The controller 170 also communicates with the electronic or digital camera 220 over a trigger signal line 174. The controller 170 receives or sends a trigger signal over the trigger signal line 174 to synchronize the integration periods, i.e., the differing time periods during which corresponding sets of camera pixels are activated to respond to the incident light, of the electronic or digital camera 220 with the light source 110 and the motor 120.

Figure 2:
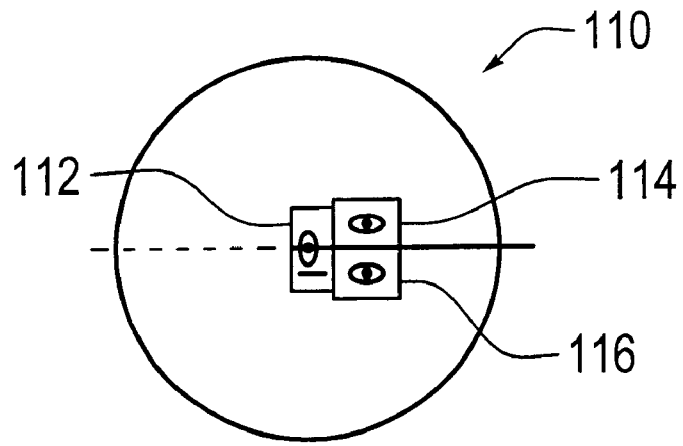
FIG. 2 is a plan view of one exemplary embodiment of a light source according to this invention.

As shown in FIG. 2, the light source 110 may include an array of solid-state devices 112, 114 and 116, each of which has different characteristics. In one exemplary embodiment, the LEDs 112–116 operate in the red, green and blue spectral regions, respectively. In another exemplary embodiment, the LEDs 112–116 can emit radiation in the near infrared or other spectral regions that are compatible with observing the sample part 300. A light source 110 having multiple solid-state devices can multiplex among the individual solid-state devices to optimally illuminate the sample part 300. In addition, a multi-wavelength addressable light source can match or avoid the average spectral absorption properties of the sample part 300 to enhance the image contrast.

Figure 3:
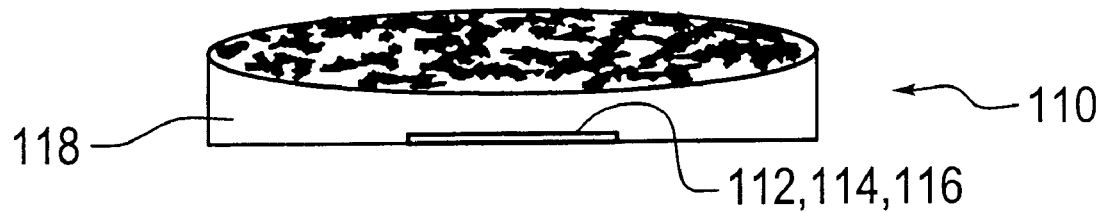
FIG. 3 is a perspective view of another exemplary embodiment of a light source according to an embodiment of this invention.

As shown in FIG. 3, the solid-state devices 112–116 may also be surface mounted in an acrylic-encapsulated package 118 to form the light source 110. For example, surface-mounted solid-state devices 112–116 can be combined with a collection and/or collimation lens to form the light source 110.

Figure 4:
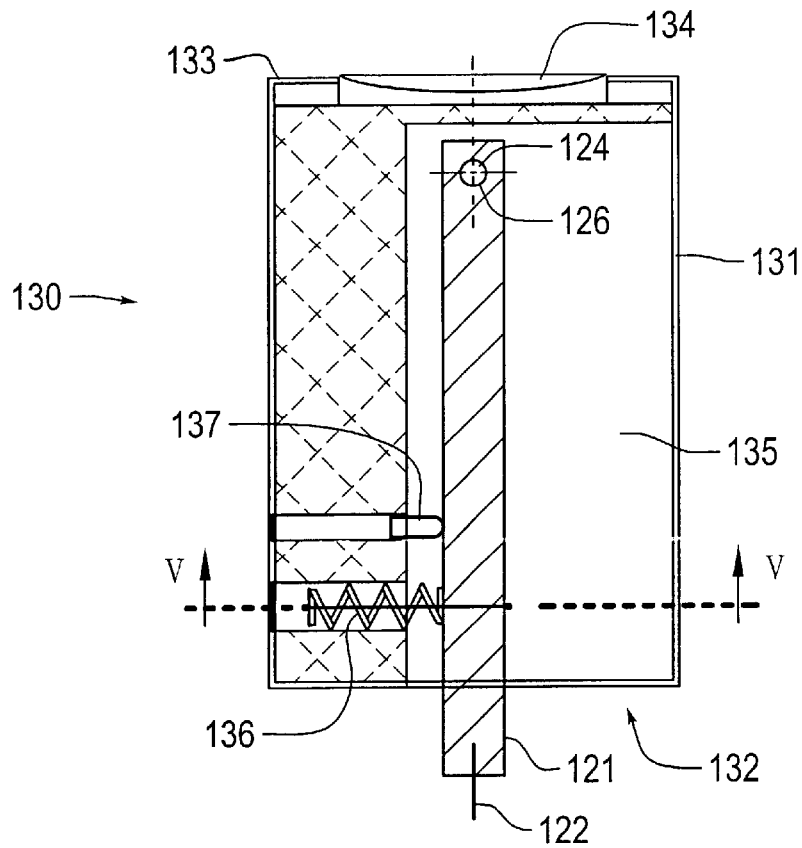
FIG. 4 is a sectional view of one exemplary embodiment of a beam deflector used to implement the light pattern controller according to this invention.

FIG. 4 shows a sectional view of a first exemplary embodiment of the light pattern controller 115 that includes the beam deflector 130 in accordance with this invention. As shown in FIG. 4, the beam deflector 130 deflects the light beam 111 from the light source 110. In this exemplary embodiment, the beam deflector 130 includes a cylindrically-shaped barrel 131 having a first end 132 and a second end 133. The mirror 134 is mounted on the second end 133. An internal cavity 135 of the beam deflector 130 defines an area in which the motor shaft 121 is received.

The motor shaft 121 is aligned with a transmitting axis 122. The motor shaft 121 also includes a hole 126 that accepts a clevis pin 124 about which the beam deflector 130 pivots.

As shown in FIG. 4, the center of mass of the beam deflector 130 is located to the left of the transmitting axis 122. Thus, when the motor shaft 121 rotates, a centrifugal force operates through the center of mass of the beam deflector 130 to push the center of mass away from the motor shaft 121.

A spring 136 within the beam deflector 130 counteracts the centrifugal force. Although the spring 136, as shown, provides a counteracting force, any known or later developed device for applying a counteracting force can be used with the beam deflector 130 in accordance with this invention.

A position adjuster 137 is disposed within the cavity 135 of the barrel 131. The position adjuster 137 adjusts an angle between the longitudinal axis of the barrel 131 and the transmitting axis 122 of the motor shaft 121 within a predetermined range. In one exemplary embodiment, the adjuster 137 adjusts the angle such that the angle is substantially equal to zero when the angular velocity of the shaft 121 is below a threshold velocity $\omega_0$.

The mirror 134 shown in FIG. 4 is a concave, spherical mirror having a center that is coincident with the transmitting axis 122. The mirror 134 may also be a planar or convex mirror. It should be understood that the mirror 134 may be any known or later developed reflector capable of reflecting electromagnetic radiation of the wavelengths emitted by the light emitting devices of the light source 110.

Figure 5:
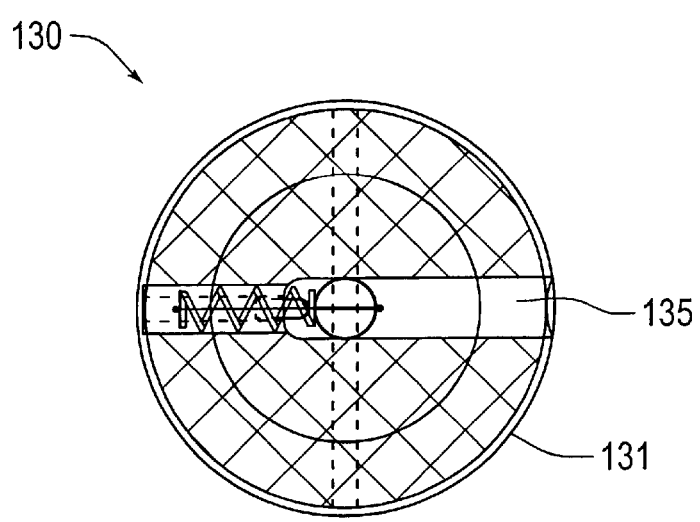
FIG. 5 is a sectional view of the beam deflector of FIG. 4 taken along line V—V.

FIG. 5 shows a sectional view of the beam deflector 130 taken through the line V—V in FIG. 4. The cavity 135 forms a transverse slot to permit the barrel 131 to pivot inside the cavity 135 about the clevis pin 124.

Accordingly, the beam deflector 130 generates two-dimensional circular patterns of light. The two-dimensional patterns of light have a variable radius that is a function of the angular velocity ω at which the beam deflector 130 rotates.

As discussed above, the mirror 134 reflects the light output by the solid-state light emitting devices of the light source 110. Furthermore, the focal length of the mirror 134 is chosen to provide a light beam having a predetermined diameter d. The focal length of the mirror 134 is also chosen based on the performance of the light source 110. The diameter d of the light beam 111 incident on the inspection plane 310 is chosen to provide adequate image brightness and field of view-conformity. For example, a mirror 134 having a diameter of approximately 12.5 mm can be used to provide a focal length of approximately 12 mm to 40 mm. The focal length of the mirror 134 is chosen to provide the clearest image of the sample part 300. The direction and/or divergence of the light beam 111 must be taken into consideration when choosing the mirror 134.

As discussed above, after the light beam 111 reflects off the mirror 150, the light beam 111 must be redirected onto the sample part 300. The focusing element 160 redirects the light beam 111 onto the sample part 300.

Figure 6:
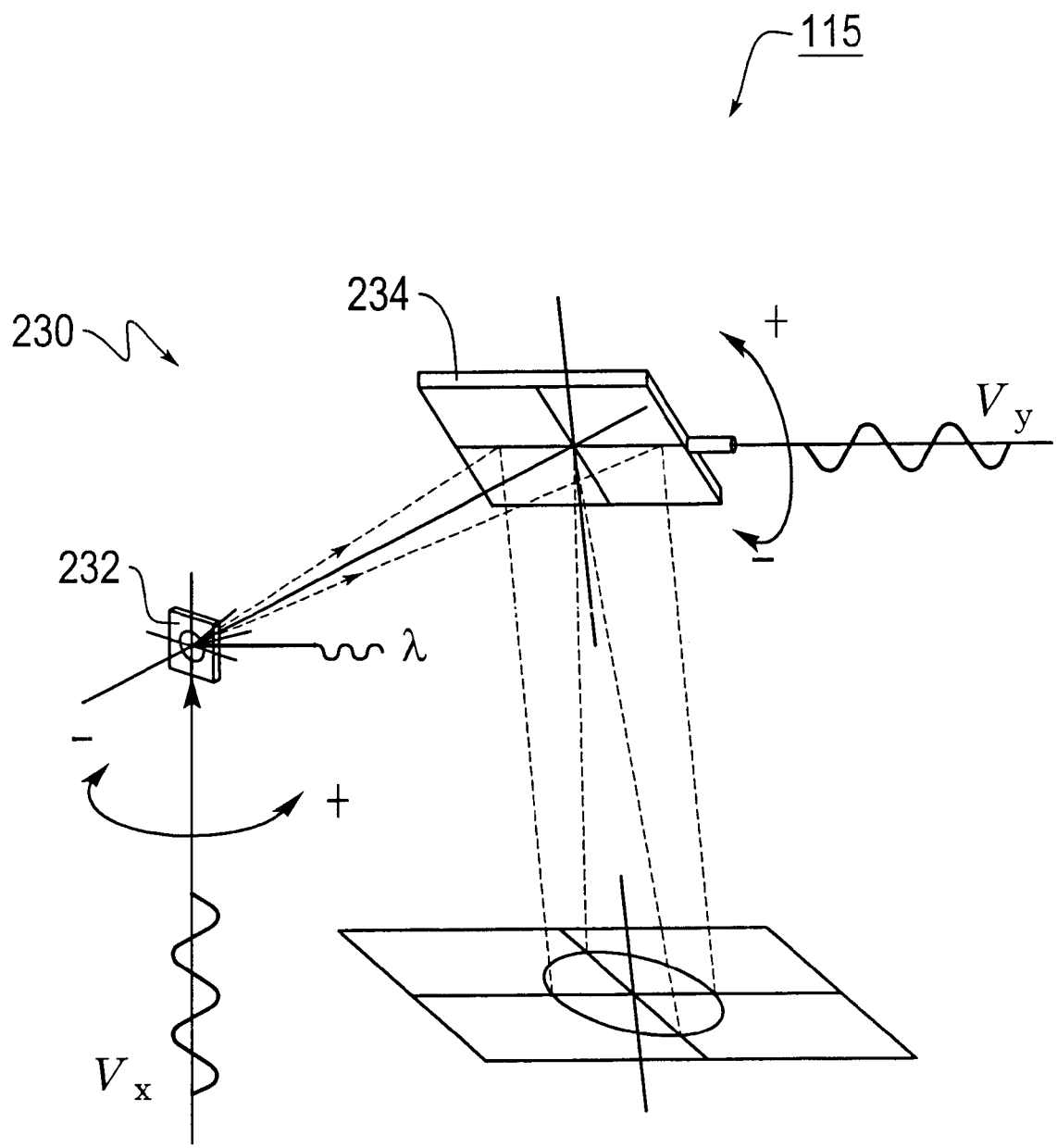
FIG. 6 shows another exemplary embodiment of a light pattern controller according to this invention.

FIG. 6 shows a second exemplary embodiment of the light pattern controller 115 which includes a second beam deflector 230 in accordance with this invention. As shown in FIG. 6, the second beam deflector 230 is a two-dimensional scanning galvanometer, and includes two angular scanning galvanometers 232 and 234. The scan axes of the two angular scanning galvanometers 232 and 234 are orthogonal to each other. To achieve illumination symmetry about the optical axis 112, the swept pattern is made circular. This circular pattern is created using the two angular scanning galvanometers 232 and 234. A circular pattern is created by input drive signals $V_x$ and $V_y$ that are input to the scanning galvanometers 232 and 234, respectively. The two scanning input drive signals are sinusoidal wave-forms described by:

$$V_x = A_x \sin(2\pi f_x t + \theta_x); \text{ and} \quad (1)$$

$$V_y = A_y \sin(2\pi f_y t + \theta_Y). \quad (2)$$

where:

$A_x$ is the fundamental or maximum amplitude of the sinusoidal input drive signal $V_y$;

$A_y$ is the fundamental or maximum amplitude of the sinusoidal input drive signal $V_y$;

$\theta_x$ is the phase angle of the sinusoidal input drive signal $V_x$ with respect to a reference sine wave;

$\theta_y$ is the phase angle of the sinusoidal input drive signal $V_y$ with respect to $V_x$;

$2\pi f_x$ is the angular scanning frequency of the x-axis galvanometer 232; and $2\pi f_y$ is the angular scanning frequency of the y-axis galvanometer 234. It should be appreciated that the sinusoidal input drive signal $V_x$ is designed to follow the reference sine wave faithfully with zero phase difference.

The scanning galvanometers 232 and 234 each tilts an amount from a rest position that corresponds to the amplitude of the corresponding drive signal $V_x$ or $V_y$. In particular, the scanning galvanometers 232 and 234 are positioned so that, when scanning galvanometers 232 and 234 are at their rest positions, the light beam from the light source 110 will be collinear with the optical axis 212. That is, the angle of incidence on both the X and Y axis will be zero. Thus, when the drive signal $V_x$ or $V_y$ has a zero amplitude, the corresponding scanning galvanometer 232 or 234 will have a zero tilt amount, i.e., a zero tilt angle, relative to the corresponding rest position. In contrast, when the drive signal $V_x$ or $V_y$ has the corresponding fundamental or maximum amplitude $A_x$ or $A_y$, the corresponding scanning galvanometer 232 or 234 will have a maximum tilt amount or tilt angle relative to the corresponding rest position.

The scanning galvanometers 232 and 234 are driven with sinusoidal drive signals $V_x$ or $V_y$ having a sine and cosine relationship. Therefore, the pattern created by driving the two angular scanning galvanometers 232 and 234 with these sinusoidal drive signals $V_x$ or $V_y$ will have an angle of incidence on the sample part 300 that corresponds to the fundamental or maximum amplitudes $A_x$ and $A_y$. If the fundamental or maximum amplitudes $A_x$ and $A_y$ are the same, the pattern will be circular and the angle of incidence of the pattern will not vary as the pattern is swept by the scanning galvanometers 232 and 234. If the fundamental or maximum amplitudes $A_x$ and $A_y$ are not the same, the pattern will be elliptical, or some other shape if the fundamental or maximum amplitudes $A_x$ and $A_y$ also vary over time, and the angle of incidence of the pattern will vary as the pattern is swept by the scanning galvanometers 232 and 234.

Additionally, to obtain a symmetric, circular pattern, the input wave-forms must be controlled such that:

$$(\theta_x - \theta_y) = \pi/2, 3\pi/2 \quad (3)$$

The drive frequencies $f_x$ and $f_y$ are controlled to provide the proper number of circular sweep cycles per video field integration in the electronic imaging elements of the electronic or digital camera 220. A minimum execution of two whole sweep cycles per field integration will minimally assure meeting the Nyquist criteria of the electronic or digital camera 220. Further, all sweep cycles per field integration should be whole numbers to ensure that, if interlaced fields are desired, interlaced fields produce spatially similar illumination patterns in assembled frames. The drive frequencies are controlled according to:

$$f_x = f_y \quad (4)$$

where:

$$f_{min} \leq f_i \leq f_{resonant} \quad (5)$$

In the case of an RS170 camera with interlaced fields operated in the frame-integration mode, $f_{min}$ is twice as fast as the overlap time period between odd and even fields. This overlap period is 16⅔ msec. Therefore, $f_{min}$ would correspond to a sweep rate occurring at least 2 times within this period or every 8⅓ msec (120 Hz). Choice of the XY scanner and the inertia of each mirror restrict the upper limit, $f_{resonant}$. Input of equivalent drive frequencies meets the final requirement for a symmetric, circular sweep pattern.

The amplitude of each wave-form is also controlled based on the angle of incidence α which is desired by the user. Essentially, the wave-form amplitudes are chosen such that:

$$A_x = A_y \quad (6)$$

where $A_i$ represents the maximum, or peak, amplitude, and thus defines the sweep circle radius, for each specific desired angle of illumination incidence α.

This radius or amplitude is selectable within the mirror scan angle range $\zeta_i$, where $-\zeta_{max} \leq \zeta_i \leq +\zeta^i_{max}$. As a result, the diameter of the circularly scanned pattern is controlled by the choice of wave-form amplitudes.

In one exemplary embodiment of the control systems of this invention, a lookup table is used to translate the angle of incidence to the input voltage values for the scanning galvanometer. As discussed with respect to the above outlined parameters, illumination conditions selected by the user dictate the specific input settings to each scanner axis.

Additionally, it should be understood that the angle of incidence can vary by sector. For example, the motor 120 may be controlled to operate at a speed which varies such that the light beam circumscribes an ellipse on the collimator 140 rather than circumscribing a circle. In this instance, the controller 170 may select a pulse repetition frequency and phase angle which places the light beam on the illumination field at angles of incidences which vary across sectors. Similarly, the two dimensional scanning galvanometer 230 may be controlled to vary the angle of incidence over time and in different sectors.

It should be understood that, while a beam deflector and a two-dimensional scanning galvanometer have been described in detail above, any known or later developed apparatus or structure for and/or method of sweeping a light pattern onto a surface of a collimator may be used.

Figure 7:
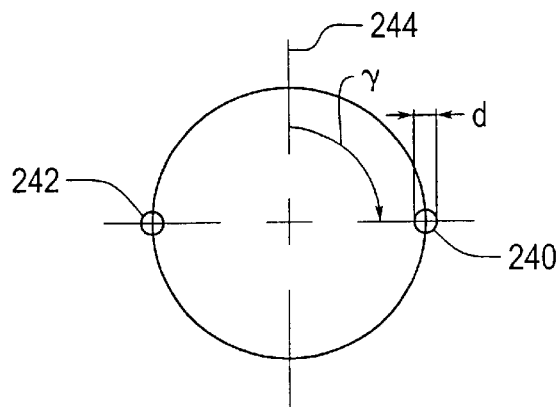
FIG. 7 is a plan view of a first exemplary illumination field in time elapse at the final focusing element.
Figure 10:
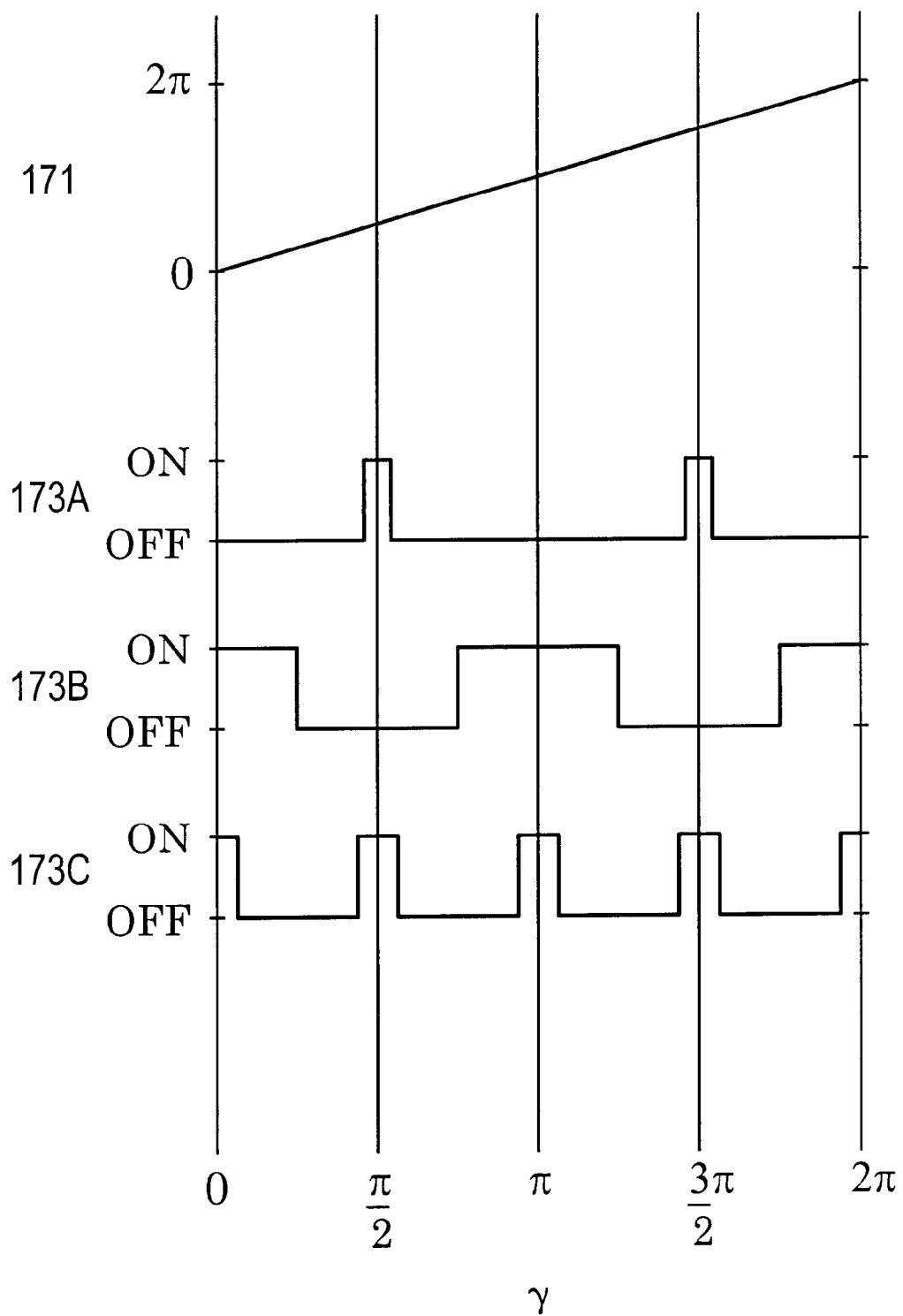
FIG. 10 is a timing diagram illustrating the illumination timing necessary to generate the first-third illumination fields shown in FIGS. 7–9.

FIG. 7 shows one exemplary illumination field in time elapse at the plane of the focusing element 160 illuminated by any exemplary embodiment of the systems and methods of this invention. FIG. 10 shows a timing diagram for the encoder signal received on the signal line 171 and a drive signal 173A that generates the illumination field shown in FIG. 7 output by the controller 170 to the light source 110. The controller 170 synchronizes the modulation or drive signal 173A output over the signal line 173 to the light source 110 with the rotational position of the beam deflector 130 or 230, as indicated by the encoder signal 171, to form the illuminated areas 240 and 242. Here, the drive signal 173A output to the light source 110 is modulated in a pulsed mode. There are two illuminated areas 240 and 242 because the timing of the drive signal to the light source 110 is set at a pulse repetition frequency that is twice the angular frequency of the beam deflector 130 or 230. As shown in FIG. 10 a pulse occurs at a position γ of π/2 and 3π/2 as determined by the encoder signal on signal line 171.

Alternatively, the drive signal output to the light source 110 could be modulated in a continuous wave (cw) mode. For example, the drive signal output to the light source 110 could be modulated as a sinusoid, triangle sawtooth, or other desired functional waveform. The illuminated areas 240 and 242 are circular because the light source 110 is driven in a pulsed mode to illuminate the sample part 300 for an instant in time, i.e., at a low duty cycle. The illuminated area 240 is at a phase angle γ of π/2 radians and the illuminated area 242 is at a phase angle γ of 3π/2 radians relative to the datum position 244 for the beam deflector.

Figure 8:
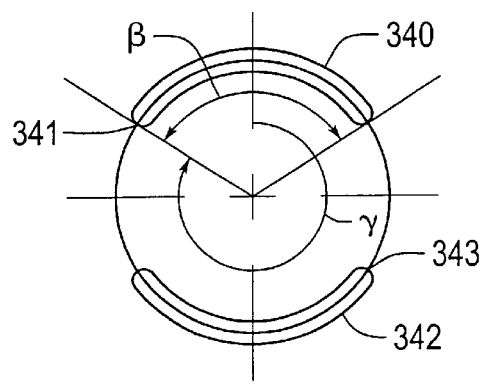
FIG. 8 is a plan view of a second exemplary illumination field in time elapse at the final focusing element.

FIG. 8 shows a second exemplary illumination field in time elapse at the plane of the focusing element 160 illuminated by any exemplary embodiment of the control systems and methods of this invention. FIG. 10 shows a timing diagram for the encoder signal received on the signal line 171 and a drive signal 173B that generates the illumination field shown in FIG. 8 output by the controller 170 to the light source 110. The controller 170 synchronizes the modulation or the drive signal 173B output over the signal line 173 to the light source 110 with the rotational position of the beam deflector 130 or 230, as indicated by the encoder signal 171, to form the illuminated areas 340 and 342.

The timing of the drive signal 173B to the light source 110 is at a pulse repetition frequency which is twice the angular frequency of the light position controller. In this example, the drive signal 173B output to the light source 110 is a square wave. Moreover, energy is delivered to the plane of the focusing element 160 half of the time. As shown in both FIGS. 8 and 10, the leading edges 341 and 343 of the illuminated areas 340 and 342 are positioned at the phase angles γ of 7π/4 and 3π/4 radians, respectively, relative to the datum point 244. The duty cycle of the light source 110 determines the arc length β of the illuminated areas 340 and 342.

Figure 9:
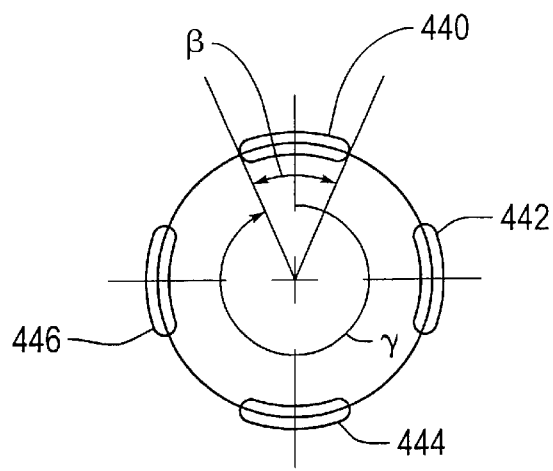
FIG. 9 is a plan view of a third exemplary illumination field in time elapse at the final focusing element.

FIG. 9 shows a third exemplary illumination field in time elapse at the plane of the focusing element 160 illuminated by any exemplary embodiment of the control systems and methods of this invention. FIG. 10 shows a timing diagram for the encoder signal received on the signal line 171 and a drive signal 173C that generates the illumination field shown in FIG. 8 output by the controller 170 to the light source 110. The controller 170 synchronizes the modulation or the drive signal 173B output over the signal line 173 to the light source 110 with the rotational position of the beam deflector 130 or 230, as indicated by the encoder signal 171, to form the illuminated areas 440, 442, 444 and 446. The illumination field of FIG. 9 has four illumination areas because the pulse repetition frequency of the light source 110 is four times the rotational frequency of the beam deflector 130 or 230. The arc length β of the illuminated areas 440, 442, 444 and 446 is approximately half the arc lengths β of the illuminated areas 340 and 342 shown in FIG. 8 because the duty cycle for the illuminated areas 440–446 is approximately half that of the illuminated areas 340 and 342 shown in FIG. 8.

In another exemplary embodiment of the systems and methods of this invention, the illumination field may be illuminated by a different color for each sector. For example, the illumination area 440 may be illuminated using a red light beam, illumination area 442 may be illuminated using a green light beam, illumination area 444 may be illuminated using a blue light beam, and illumination area 446 may be illuminated using a light beam having yet another color. It should be understood that the hue and intensity of the color of the light beam emitted by any particular solid-state light emitting device can be controlled by the controller 170 and may be varied by sector and/or by time.

In operation, a desired phase angle, γ; a desired arc length, β; and a desired angle of incidence, α are input to the controller 170. In response, the controller 170 sends a drive signal over the signal line 172 to the motor 120 to drive the motor 120 at a rotational speed ω which provides the desired angle of incidence of α. The controller 170 also outputs a modulated drive signal over the signal line 173 to the light source 110 to drive the solid-state light emitting devices of the light source 110 at a pulse repetition frequency, pulse width, i.e., duty cycle, and phase angle that cause the emitted light beams to illuminate the sample part 300 at the desired phase angle γ and over the desired arc length β.

Figure 11:
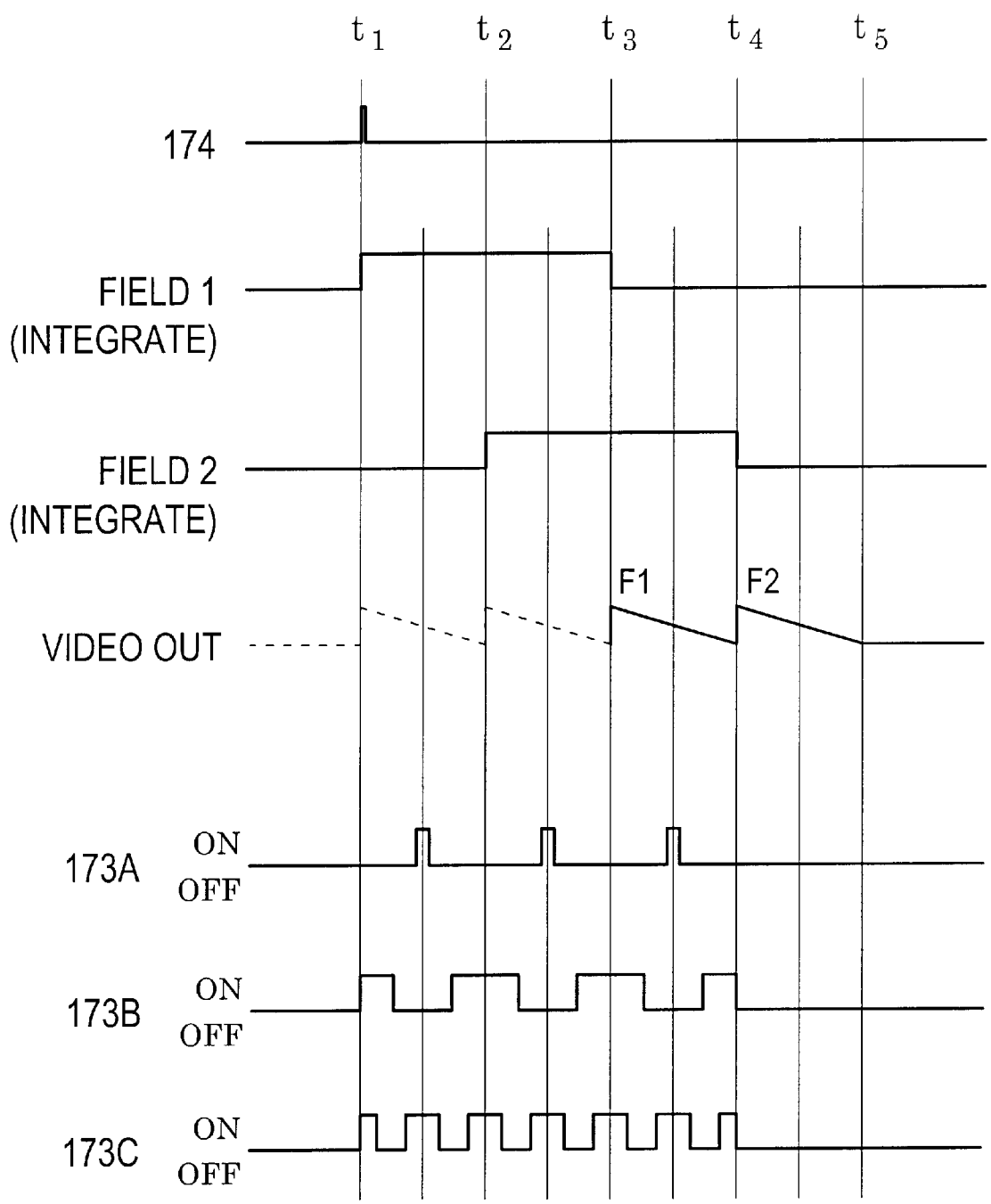
FIG. 11 is a timing diagram illustrating how the illumination timing is synchronized with the frame capture timing according to one exemplary embodiment of the systems and methods of this invention.

FIG. 11 shows a timing diagram illustrating how the illumination timing is synchronized with the frame capture timing according to one exemplary embodiment of the systems and methods of this invention. The signals "field 1" and "field 2" each represent an integration period for an electronic camera 220 operated in the interlaced, frame-integration mode, i.e., maximum vertical resolution. Alternatively, the electronic camera 220 could be operated in either an interlaced field-integration mode or an non-interlaced field-integration mode. The first field of the electronic camera 220, controlled by the integration signal "field 1", begins integrating light at a first time $t_1$ and stops integrating at a third time $t_3$. The second field of the electronic camera 220, controlled by the integration signal "field 2", begins integrating light at a second time $t_2$ and stops integrating at a fourth time $t_4$. The "video out" signal represents the formatted video signal produced by the electronics in the camera 220. Between the third and fourth times $t_3$ and $t_4$, the video out signal outputs the integrated data of the first field. Between the fourth time $t_4$ and a fifth time $t_5$, the video out signal outputs the integrated data of the second field.

The amount of illumination, or light energy, received by each of the first and second fields of the electronic camera 220 should be the same. Otherwise, every line of the image resulting from interlacing the fields will have a different average light intensity than the immediately adjacent lines above and below that line. Such differing average light intensity values will make it difficult, if not impossible, to correctly analyze the resulting image.

In order to balance the light received by each of the first and second fields of the electronic camera 220, the systems and methods of this invention control the light pattern controller 115 such that the same number of each illumination pattern created by the light pattern controller 115 are generated during each integration period. For example, when the light pattern controller 115 is the beam deflector 130 or the two dimensional scanning galvanometer 230, and the light pattern controller 115 generates the illuminated areas 340 and 342, the light pattern controller is controlled to sweep the light beam so that the same number of illuminated areas 340 occur during each integration period. Similarly, the light pattern controller is controlled to sweep the light beam so that the same number of illuminated areas 342 occur during each integration period.

Generally, the same number of illuminated areas 340 and 342 occur during each integration period, so that the illumination intensity resulting from each illumination area is the same. However, the same illumination intensity, while usually desired, is not mandatory, such that the number of illuminated areas 340 occurring during each integration period does not need to be the same as the number of illuminated areas 342 occurring during each integration period.

The simplest way to ensure that the same number of each illumination pattern occurs during each integration period is to control the integration period of the electronic camera 220 or the rotation rate of the beam deflector 130 or the two dimensional scanning galvanometer 230 so that an integer number of rotations of the beam deflector 130 or the two dimensional scanning galvanometer 230 occur during each integration period. However, it should be appreciated that while this is the simplest way to ensure that the same number of each illumination pattern occurs during each integration period, non-integer numbers of rotations of the beam deflector 130 or the two dimensional scanning galvanometer 230 can be used.

For example, for the illumination areas 340 and 342 shown in FIG. 8, the integration period of the electronic camera 220 or the rotation rate of the beam deflector 130 or the two dimensional scanning galvanometer 230 must be controlled so that, if the integration period of one of the patterns begins at the phase position $7\pi/4$, the integration period for the first field should extend over between (x+7/8) rotations and 2x rotations to record (x+1) full occurrences of each illumination area 340 and 342. Then, if the integration period for the second field also extends over between (x+7/8) rotations and 2x rotations, the second field will begin at the phase position $(x\pi+5\pi/8)$ and will also record (x+1) full occurrences of each illumination area 340 and 342.

In the exemplary embodiment of the synchronization timing diagram shown in FIG. 11, each time $t_{x+1}$ occurs a time period dx after the preceding time $t_x$. In one exemplary embodiment of the electronic camera 220 according to this invention, the time period dx is 16 and ⅔ milliseconds. Thus, the integration period for each field is 33 and ⅓ milliseconds.

As shown in FIG. 11, in the exemplary embodiments of the system 100 shown in FIGS. 1 and 5, the controller 170 receives a reference position signal from the beam deflector 130 over the signal line 171 each time the beam deflector 130 rotates past a reference position. In the synchronization timing diagram shown in FIG. 11, this reference position corresponds to the position 244 shown in FIGS. 7–9. This reference position signal allows the controller 170 to monitor the rotational position of the beam deflector 130 and control the rotational speed of the beam deflector 130.

The controller 170 can use this to generate a control signal sent over the signal line 172 to speed up or slow down the rotational speed of the beam deflector 130 so that the beam deflector will be at a desired phase position (or positions) relative to the rising edges of the integration signals field 1 and field 2. Alternatively, the controller 170 can use this to generate a control signal sent over the signal line 174 to the electronic or digital camera 220 to trigger the rising edge of the first integration signal field 1 at or before the beam deflector 130 reaches the desired phase position. The desired phase position is generally the leading edge of one of the illumination areas of the light pattern. It should also be appreciated that the controller 170 can control both the rotational speed of the beam deflector 130 and the triggering of the integration period of the first field of the electronic or digital camera 220, depending on the integration mode of operation.

The controller 170 also generates speed control signals that are sent over the signal line 172 to the motor 120 to control the rotational speed of the beam deflector 130 to ensure an equal number of each illumination area is produced for each field of the electronic camera 220 during the integration period for each field. Most simply, the controller 170 controls the rotational speed of the beam deflector 130 so that an integer number of rotations occur during each 33⅓ millisecond frame integration period, i.e., a rotational speed of (1800·z) revolutions per minute or (30·z) revolutions per second, where z is the integer number of rotations occurring during each integration period.

However, it should be appreciated that, as described above, a particular rotational speed of the beam deflector 130 may be necessary to obtain a desired angle of incidence α. In this case, the rotational speed of the beam deflector 130 can be rounded to the nearest multiple of 1800 revolutions per minute (30 revolutions per second). Alternatively, if the integration period of the electronic or digital camera 220 can be adjusted, the controller could output a frame integration period adjustment signal over the signal line 174 to the electronic or digital camera 220. Thus, in this case, the integration period of the electronic or digital camera 220 is adjusted so that an integer number of rotations of the beam deflector 130 at the particular rotational speed needed to obtain the desired angle of incidence a will occur during the adjusted integration period.

It should also be appreciated, as described above, that the controller 170 could determine that, for the particular rotational speed needed to obtain the desired angle of incidence a, an equal number of each illumination area will occur during the standard integration period for both the first and second fields, even if an integer number of rotations of the beam deflector 130 will not occur during the standard integration period. In this case, the controller 170 could control the timing of the rising edge of the first integration signal field 1 so that an equal number of each illumination area will occur during the standard frame integration period for both the first and second fields.

FIG. 11 also shows the relative timings between the trigger signal output from the controller 170 to the camera 220 on the signal line 174, the integration signals field 1 and field 2, and the drive signals 173A–173C output over the signal line 173 to the light source 110. The drive signals 173A–173C are the same as the drive signals 173A–173C shown in FIG. 10 and correspond to the light patterns shown in FIGS. 7–9, respectively.

As shown in FIG. 11, when the camera is operated in a frame-integration mode, the rising edge of the first integration signal field 1 is output by the camera 220 to the controller 170 over the signal line 174. The controller 170 has previously determined the necessary illumination pattern to be generated by the drive signal output over the signal line 173 to the light source 110 and the relative phase position of the beam deflector 130 to the reference position 244 shown in FIGS. 7–9.

To create the illumination pattern shown in FIG. 7, the controller 170 outputs the drive signal 173A to the light source 110. In particular, as shown in FIG. 11, assuming the beam deflector is rotating at 30 revolutions per second, the drive signal 173A goes high momentarily at approximately 8.33 milliseconds and 25 milliseconds after the rising edge of the first integration signal field 1 during the first integration period. The drive signal 173A is also high momentarily during the second integration period at approximately 25 and 41.67 milliseconds after the rising edge of the first integration signal field 1. Accordingly, one illumination area 240 and one illumination area 242 occur during each integration period.

To create the illumination pattern shown in FIG. 8, the controller 170 outputs the drive signal 173B to the light source 110. In particular, as shown in FIG. 11, assuming the beam deflector is rotating at 30 revolutions per second, the drive signal 173B goes high immediately with the rising edge of the first integration signal field 1 and remains on for approximately 4.17 milliseconds before turning off. The drive signal 173B then goes high at approximately 12.5 milliseconds and 29.17 milliseconds after the rising edge of the first integration signal field 1, remaining on for approximately 8.33 milliseconds each time. The drive signal 173B is on when the second integration signal field 2 goes high and remains on for 4.17 milliseconds. The drive signal 173B also goes high during the second integration period at approximately 29.17 and 45.83 milliseconds after the rising edge of the first integration signal field 1, remaining on for approximately 8.33 and 4.17 milliseconds each time, respectively.

Accordingly, one illumination area 340 and one illumination area 342 occur during each integration period. In particular, a second half of the illumination area 340 occurs at the beginning of the first integration period, the illumination area 342 occurs during the middle of the first integration period, and the first half of the illumination area 340 occurs at the end of the first integration period. Similarly, a second half of the illumination area 342 occurs at the beginning of the second integration period, the illumination area 340 occurs during the middle of the second integration period, and the first half of the illumination area 342 occurs at the end of the second integration period.

It should be appreciated that, if for any reason it is desirable to avoid breaking up the illumination areas of the illumination pattern in this way, the relative timing of the rising edge of the first integration signal field 1 to the leading edges of the illumination areas can be adjusted. For example, for the illumination pattern shown in FIG. 8, when the camera is operated in a field-integration mode, the rising edge of the first integration signal field 1 could be delayed to occur between approximately 4.2 milliseconds and approximately 12.4 milliseconds. That is, the rising edge of the first integration signal field 1 could be delayed to occur between the trailing edge of the illumination area 340 and the leading edge of the illumination area 342.

To create the illumination pattern shown in FIG. 9, the controller 170 outputs the drive signal 173C to the light source 110. In particular, as shown in FIG. 11, assuming the beam deflector is rotating at 30 revolutions per second, the drive signal 173C goes high immediately with the rising edge of the first integration signal field 1 and remains on for approximately 2.08 milliseconds. The drive signal 173B then goes high at approximately 6.25 milliseconds, 14.48 milliseconds, 22.92 milliseconds and 31.24 milliseconds after the rising edge of the first frame integration signal field 1, remaining on for approximately 4.17 milliseconds each time. The drive signal 173B is on when the second integration signal field 2 goes high and remains on for 2.08 milliseconds. The drive signal 173B also goes high during the second integration period at approximately 22.92 milliseconds, 31.24 milliseconds, 39.58 milliseconds and 47.92 milliseconds after the rising edge of the first integration signal field 1, remaining on for approximately 4.17 milliseconds each time, except for the last interval, which requires that the drive signal 173B be high for only 2.08 milliseconds.

Accordingly, one illumination area 440, one illumination area 442, one illumination area 444, and one illumination area 446 occur during each integration period. In particular, a second half of the illumination area 440 occurs at the beginning of the first integration period, the illumination areas 442–446 occur during the middle of the first integration period, and the first half of the illumination area 440 occurs at the end of the first integration period. Similarly, a second half of the illumination area 444 occurs at the beginning of the second integration period, the illumination areas 440, 442 and 446 occur during the middle of the second integration period, and the first half of the illumination area 444 occurs at the end of the second integration period.

Figure 12:
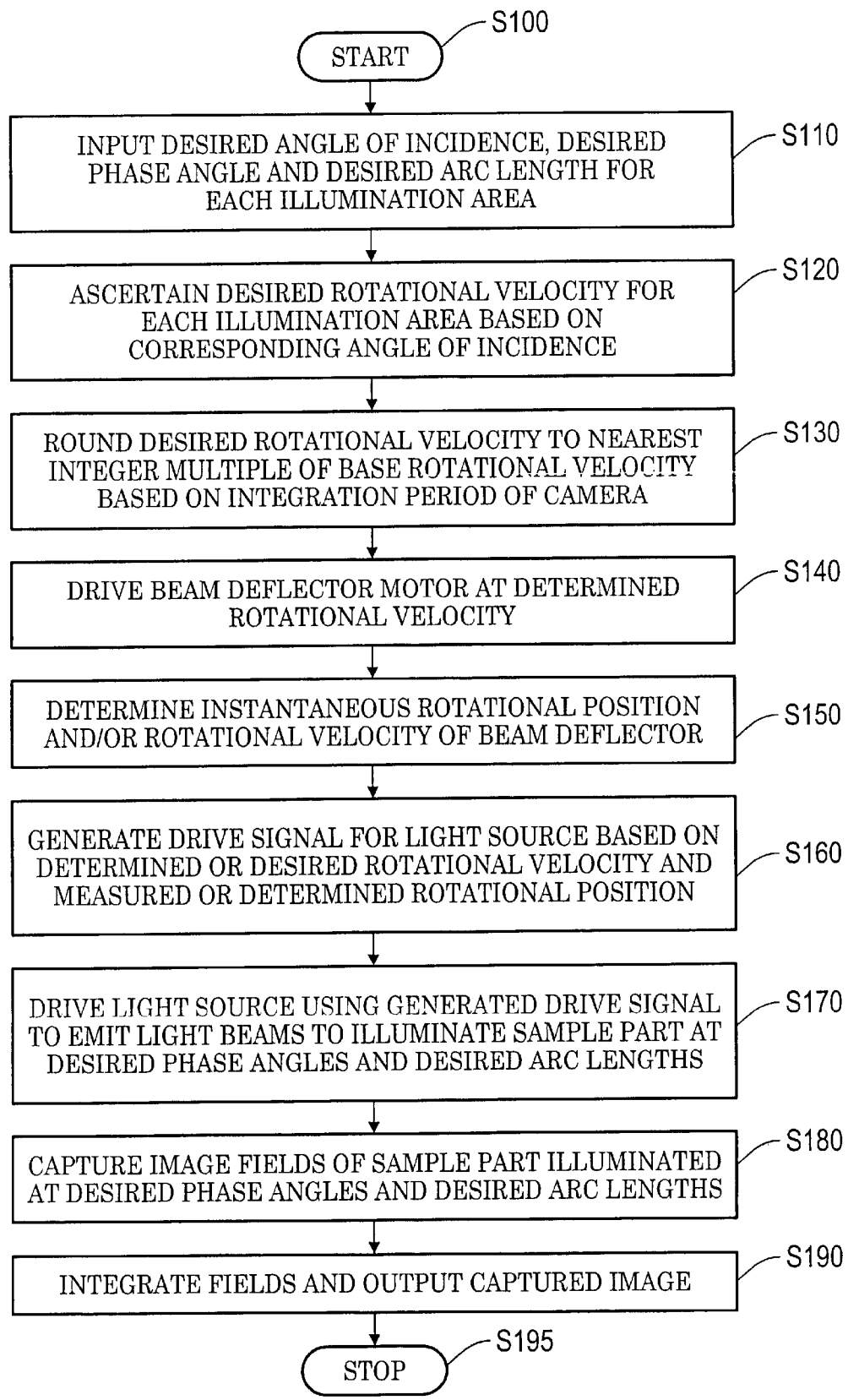
FIG. 12 is a flowchart outlining one exemplary embodiment of the control methods according to this invention.

FIG. 12 is a flowchart outlining one exemplary embodiment of the control methods according to this invention. Beginning in step S100, control continues to step S110, where a desired phase angle γ of the leading edge of each illuminated area, a desired arc length β of each illuminated area, and a desired angle of incidence α of each illuminated area are input. Next, in step S120, the desired rotational velocity ω at which the motor will provide the desired angles of incidence is ascertained. Then, in step S130, the desired rotational velocity is rounded to the nearest integer multiple of a base rotational velocity that is determined from the integration period of the camera. This ensures that the beam deflector 130 rotates an integer number of times during each integration period. Control then continues to step S140.

In step S140, the motor is driven to rotate at the rounded rotational velocity ω that provides approximately the desired angles of incidence α input in step S110. Then, in step S150, the instantaneous position, and/or the instantaneous rotational velocity, of the motor is determined. Next, in step S160, the drive signal for the light source is generated based on either the measured rotational velocity or the rounded desired motor velocity ω, and on either a determined motor position or the measured motor position. Control then continues to step S170.

In step S170, a trigger signal is output by or to the camera to indicate the beginning of the first integration period. When the camera is operated in a frame-integration mode, the trigger signal also will cause the camera to start the second integration period halfway through the first integration period. Next, in step S180, the light source is driven using the generated drive signal to emit a light beam to illuminate the sample part at the desired phase angle γ and over the desired arc length β for each illuminated area. In particular, the drive signal is output at a time when the first and second fields are able to sense the illuminated part and when the beam deflector is in the proper rotational position to create an illumination area having the corresponding desired phase angle γ and the corresponding desired arc length β. Next, in step S185, the first and second fields of the camera capture an image of the illuminated part that is illuminated over integer multiples of each of the desired illumination areas. Control then continues to step S190.

In step S190, the fields are read out to yield a full image and the image is output or displayed. Then, in step S195, the control routine stops.

Figure 13:
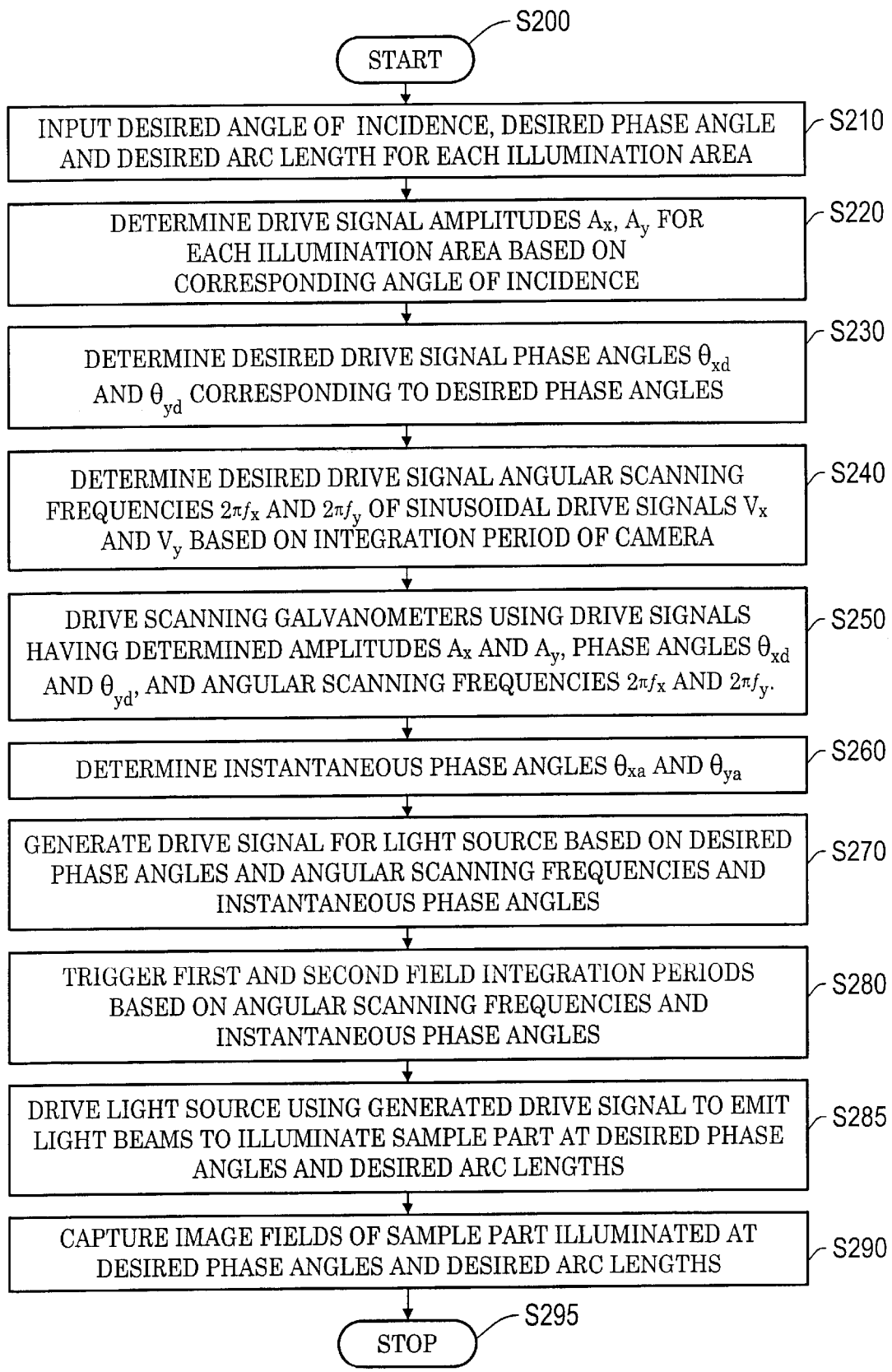
FIG. 13 is a flowchart outlining another exemplary embodiment of the control methods according to this invention.

FIG. 13 is a flowchart outlining another exemplary embodiment of the control methods of this invention. Beginning in step S200, control continues to step S210, where a desired phase angle γ of the leading edge of each illuminated area, a desired arc length β of each illuminated area, and a desired angle of incidence a of each illuminated area are input. Next, in step S220, the amplitudes $A_x$ and $A_y$ for the drive signals $V_x$ and $V_y$ input to the scanning galvanometers necessary to obtain the desired angles of incidence a are determined. Then, in step S230, the desired phase angles $\theta_{xd}$ and $\theta_{yd}$ of the sinusoidal input drive signals $V_x$ and $V_y$ necessary to obtain the desired phase angles y are determined. Control then continues to step S240.

In step S240, the instantaneous angular scanning frequencies $2\pi f_x$ and $2\pi f_y$ of the sinusoidal input drive signals $V_x$ and $V_y$ are determined based on the integration period of the camera. In particular the instantaneous angular scanning frequencies $2\pi f_x$ and $2\pi f_y$ of the sinusoidal input drive signals $V_x$ and $V_y$ are determined so that the reflected light beam from the scanning galvanometers circles an integer number of times during each integration period. Then, in step S250, the scanning galvanometers are driven using the drive signals $V_x$ and $V_y$ having the parameters determined in steps S220, S230, and S240. Next, in step S260, the instantaneous phase angles $\theta_{xa}$ and $\theta_{ya}$ of the sinusoidal input drive signals $V_x$ and $V_y$ are determined. Control then continues to step S270.

In step S270, the drive signal for the light source is generated based on desired phase angles $\theta_{xd}$ and $\theta_{yd}$, the instantaneous phase angles $\theta_{xa}$ and $\theta_{ya}$, and the instantaneous angular scanning frequencies $2\pi f_x$ and $2\pi f_y$. Next, in step S275, a trigger signal is output by or to the camera to indicate the beginning of the first integration period. When the camera is operated in a frame-integration mode, the trigger signal also will cause the camera to start the second integration period halfway through the first integration period. Then, in step S280, the light source is driven using the generated drive signal to emit a light beam to illuminate the sample part at the desired phase angle γ and over the desired arc length β. In particular, the drive signal is output at a time when the scanning galvanometers are in the proper positions to create an illumination area having the desired phase angle γ and the desired arc length β. Control then continues to step S285.

In step S285, the first and second fields of the camera capture an image of the illuminated part that is illuminated over integer multiples of each of the desired illumination areas. Then, in step S190, the fields are read out to yield a full image and the image is output or displayed. Next, in step S195, the control routine stops.

Figure 14:
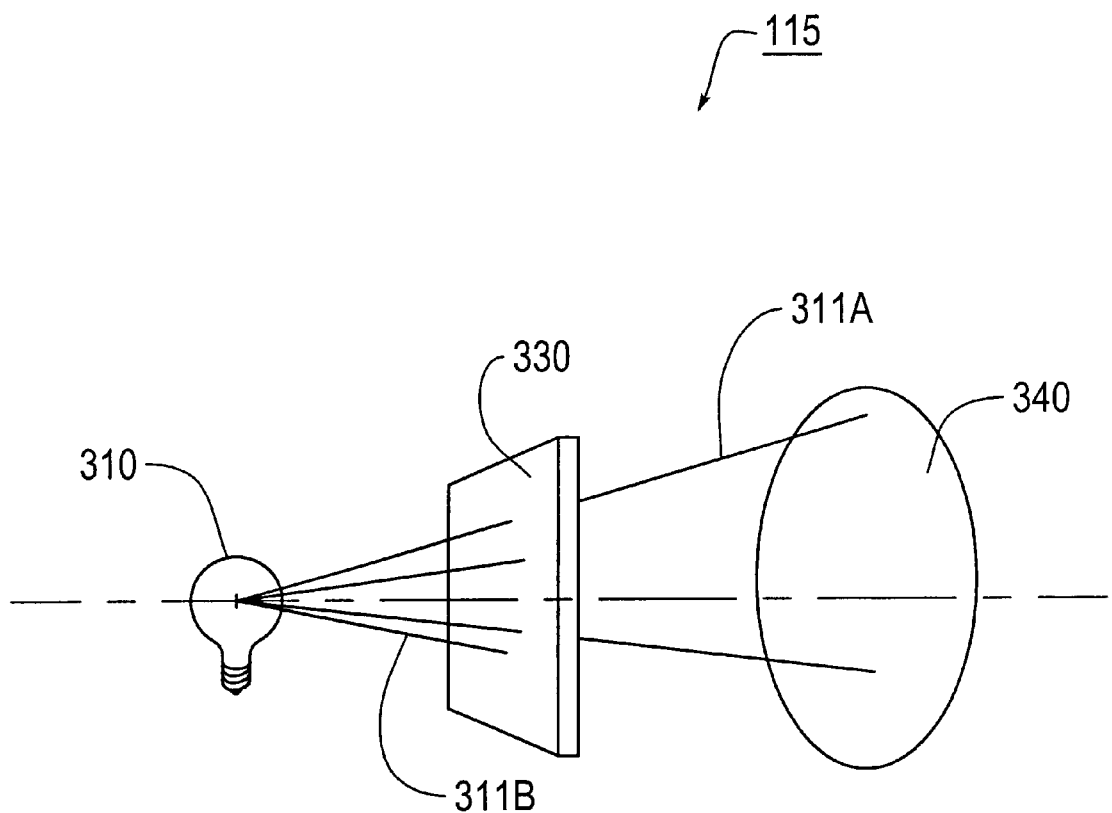
FIG. 14 shows another exemplary embodiment of light pattern controller according to this invention.

FIG. 14 shows another exemplary embodiment of the light pattern controller 115. As shown in FIG. 14, in this exemplary embodiment, the light pattern controller 115 includes a liquid crystal device 330. In particular, the liquid crystal light pattern controller 330 is a transmitting type liquid crystal device, or a liquid crystal shutter. The light source 310 emits a diverging light stream which impinges on the liquid crystal light pattern controller 330. The liquid crystal light pattern controller 330 includes an array of addressable sectors that are controllable to block portions of the light from the light source 310 from impinging on the collimator 340. For example, a light ray 311A impinges on the liquid crystal light pattern controller 330 and passes through to impinge on and be collimated by the collimating element 340. By contrast, a light ray 311B impinges on the liquid crystal light pattern controller 330 but is blocked. Thus, the light ray 311B is prevented from passing through and impinging on the collimator 340. Therefore, the liquid crystal light pattern controller 330 controls the pattern of light from the light source 310 that impinges on the collimator 340.

It should be appreciated that the addressable sectors of the exemplary liquid crystal device 330 can be in any desired shape, such as a square pixel-like shape or an arcuate sector-like shape. It should also be understood that the liquid crystal device may also include an array of addressable pixels and may also operate in a reflective mode rather than the blocking mode described above.

Figure 15:
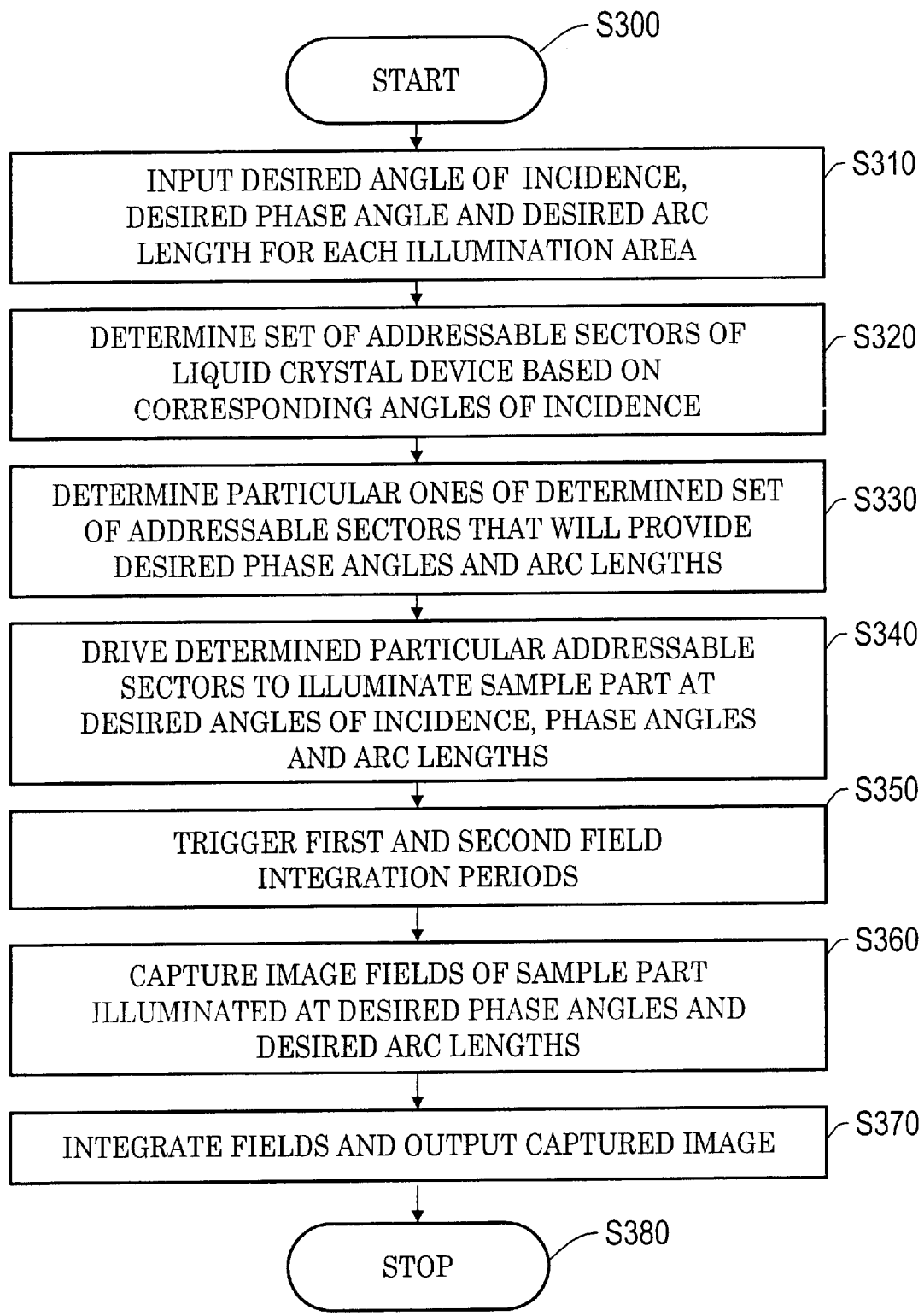
FIG. 15 is a flowchart outlining another exemplary embodiment of the control methods according to this invention.

FIG. 15 is a flowchart outlining another exemplary embodiment of the control methods of this invention. Beginning in step S300, control continues to step S310, where a desired phase angle γ of the leading edge of each illuminated area, a desired arc length β of each illuminated area, and a desired angle of incidence α of each illuminated area are input. Next, in step S320, the ring of addressable sectors of the liquid crystal light pattern controller that will provide the desired angles of incidence α for the illuminated areas is determined. Then, in step S330, the particular ones of the determined ring of addressable sectors that will provide the desired phase angles γ and arc lengths β of each of the illuminated areas are determined. Control then continues to step S340.

In step S340, the determined particular ones of the addressable sectors are driven to either pass the light incident on the liquid crystal light pattern controller, if the liquid crystal light pattern controller is a liquid crystal shutter, or to reflect the light incident on the liquid crystal light pattern controller, if the liquid crystal light pattern controller is a reflective liquid crystal device, to the collimator. Then, in step S350, a trigger signal is output by or to the camera to indicate the beginning of the first integration period. When the camera is operated in a frame-integration mode, the trigger signal also will cause the camera to start the second integration period halfway through the first integration period. Next, in step S360, the first and second fields of the camera capture an image of the illuminated part. Control then continues to step S370.

In step S370, the fields are read out to yield a full image and the image is output or displayed. Then, in step S380, the control routine stops.

Additionally, it should be understood that the angle of incidence can be varied by sector. For example, the motor 120 may be controlled to operate at a speed which varies such that the light beam circumscribes an ellipse on the collimator 140 rather than circumscribing a circle. In this instance, the controller 170 may select a pulse repetition frequency and phase angle which places the light beam on the illumination field at angles of incidences which vary across sectors. Similarly, the two dimensional scanning galvanometer 230 may be controlled to vary the angle of incidence over time and in different sectors.

While the description set forth above refers generally to light being emitted from a light source having a solid-state light emitting device, it should be understood that the systems and methods according to this invention may also use a more conventional light source, such as a tungsten halogen lamp. Additionally, it should be understood that the light source used in the systems and methods of this invention may also emit radiation outside of the visible spectrum in useful spectral regions capable of being sensed. Specifically, these spectral regions include the ultra-violet A and near infra-red portions of the spectrum. The systems and methods of this invention can also control the light source to emit a continuous wave light beam, a modulated light beam and a pulsed light beam.

While this invention has been described in conjunction with the specific embodiments outlined above, it is evident that many alternatives, modifications and variations are apparent to those skilled in the art. Accordingly, the embodiments of the invention as set forth above are intended to be illustrative and not limiting. Various changes may be made without departing from the spirit and scope of the invention.

What is claimed is:

1. An apparatus for generating an image of a diffusely illuminated object, the apparatus comprising:
    a light pattern generation system that controllably generates a pattern of light over a period of time, the pattern of light usable to illuminate the object and having at least one illumination area, each illumination area having an angle of incidence controlled independently of the illumination area for the corresponding light illuminating the object;
    a camera that has at least a first camera field having a first integration period for accumulating received light signals and a second camera field having a second integration period for accumulating received light signals; and
    a controller that synchronizes the pattern of light generated by the light pattern generation system and the at least first and second integration periods such that each camera field accumulates received light signals which correspond to a substantially identical spatial distribution and amount of the light illuminating the object.

2. The apparatus of claim 1, wherein the controller synchronizes at least one of a deflector and a modulation of a light source of the light pattern generation system with the integration periods for the at least first and second integration periods.

3. The apparatus of claim 1, wherein the controller synchronizes the at least first and second integration periods with at least one of a deflector and a modulation of a light source of the light pattern generation system.

4. The apparatus of claim 1, wherein the pattern of light is generated an integer number of times during each of the at least first and second integration periods.

5. The apparatus of claim 1, wherein the first and second integration periods at least partially overlap in time.

6. The apparatus of claim 5, wherein first and second camera fields captured during a single cycle comprising one first integration period and one second integration period are combined to generate images usable for high resolution observation and analysis of the illuminated object.

7. The apparatus of claim 1, wherein each illumination area further has at least one of a controlled phase angle and a controlled arc length of the pattern of light illuminating the object.

8. A machine vision system comprising:
    a controllable light source that outputs a modulated light beam;
    a controllable deflector that deflects the light beam from the light source to sweep out a pattern of at least one illumination area on a face of a collimating element that collimates the patterned light beam;
    a focusing element that focuses the collimated patterned light beam to illuminate an object, each at least one illumination area thereby illuminating the object with a corresponding angle of incidence, phase angle and arc length;
    a camera having at least first camera field having a first integration period for accumulating received light signals and a second camera field having a second integration period for accumulating received light signals, the camera capturing an image of the illuminated object; and
    a controller that synchronizes integration periods for the at least first and second camera fields, modulation of the light beam and the deflector so that each of the first and second fields accumulates received light signals which correspond to a substantially identical spatial distribution and amount of the light illuminating the object such that first and second camera fields captured during a single cycle comprising one first integration period and one second integration period are combinable to generate images usable in the machine vision system for high resolution observation and analysis of the illuminated object.

9. The system of claim 8, wherein the controller synchronizes the deflector and the modulation of the light beam with the integration periods for the at least first and second fields.

10. The system of claim 8, wherein the controller synchronizes the integration periods for the at least first and second fields with the deflector and the modulation of the light beam.

11. The system of claim 8, wherein the pattern is swept by the deflector an integer number of times during each integration period of the at least first and second fields.

12. A method for generating an image of a controllably diffusely illuminated object, the method comprising:
    controllably generating a pattern of light usable to illuminate the object, the pattern of light having at least one illumination area, each illumination area having an angle of incidence controlled independently of the illumination area for the corresponding light illuminating the object;
    illuminating the object with the corresponding light and imaging the object onto a camera having at least first camera field having a first integration period for accumulating received light signals and a second camera field having a second integration period for accumulating received light signals; and
    synchronizing at least the controlled angle of incidence of the corresponding light illuminating the object for each illumination area and the at least first and second integration periods so each of the at least first and second integration periods accumulates received light signals which correspond to a substantially identical spatial distribution and amount of the light illuminating the object.

13. The method of claim 12, wherein:

controllably generating the pattern of light comprises:
controllably operating a light deflector, and
controllably modulating a light beam; and synchronizing at least one of the controlled angle of incidence, a controlled phase angle and a controlled arc length of the corresponding light illuminating the object and the at least first and second integration periods comprises synchronizing at least one of the light deflector and the modulation of the light beam with the at least first and second integration periods.

14. The method of claim 12, wherein:

controllably generating the pattern of light comprises:
controllably operating a light deflector, and
controllably modulating a light beam; and synchronizing at least one of the controlled angle of incidence, a controlled phase angle and a controlled arc length of the corresponding light illuminating the object and the at least first and second integration periods comprises synchronizing the at least first and second integration periods with at least one of the light deflector and the modulation of the light beam.

15. The method of claim 12, herein each of the at least first and second integration periods accumulates received light signals which correspond to generating an integer number of each at least one illumination area during each of the first and second integration periods, respectively.

16. The method of claim 12, wherein the at least first and second integration periods overlap in time.

17. The method of claim 12, wherein first and second camera fields captured during a single cycle comprising one first integration period and one second integration period are combined to generate an image usable for high resolution observation and analysis of the illuminated object.

18. The method of claim 12, wherein each illumination area further corresponds to at least one of a controlled phase angle and a controlled arc length for the corresponding light illuminating the object and the step of synchronizing at least the controlled angle of incidence further comprises synchronizing at least one of the controlled phase angle and the controlled arc length of the corresponding light illuminating the object for each illumination area.

19. A method for generating an image by diffusely illuminating an object, comprising:

modulating a light beam;

deflecting the modulated light beam to sweep out an illumination pattern;

collimating the deflected light beam;

focusing the collimated light beam onto the object;

receiving the light reflected from the object with a camera having at least a first integration period for accumulating received light signals and a second integration period for accumulating received light signals; and synchronizing each of the first and second integration periods with modulating the light beam and deflecting the modulated light beam so that each of the at least first and second integration periods accumulates received light signals which correspond to a substantially identical spatial distribution and amount of the light illuminating the object.

20. The method of claim 19, wherein each of the at least first and second integration periods accumulates received light signals which correspond to sweeping out the illumination pattern an integer number of times during each of the first and second integration periods, respectively.

21. The method of claim 19, wherein the at least first and second integration periods overlap in time.

22. The method of claim 19, wherein received light signals captured during a single cycle comprising one first integration period and one second integration period are combined to generate an image usable for high resolution observation and analysis of the illuminated object.

* * * * *